United States Statutory Invention Registration [19]

[11] Reg. Number: H545

Mausner et al. [43] Published: Nov. 1, 1988

[54] IN VIVO GENERATOR FOR RADIOIMMUNOTHERAPY

[75] Inventors: Leonard F. Mausner, Stony Brook; Suresh G. Srivastava, Setauket; Rita F. Straub, Brookhaven, all of N.Y.

[73] Assignee: The United States of America as represented by the United States Department of Energy, Washington, D.C.

[21] Appl. No.: 114,914

[22] Filed: Oct. 30, 1987

[51] Int. Cl.[4] ..... A61K 43/00; A61K 39/395; A61N 5/00

[52] U.S. Cl. ..... 424/1.1; 424/85.91

[58] Field of Search ..... 424/11

[56] References Cited

U.S. PATENT DOCUMENTS

| | | | |
|---|---|---|---|
| 3,663,177 | 5/1972 | Arino et al. | 424/11 |
| 4,550,508 | 2/1985 | Srivastava et al. | 424/1.1 |
| 4,665,897 | 5/1987 | Lemelson | 424/1.1 |
| 4,707,440 | 11/1987 | Stavrianopoulos | 424/1.1 |

*Primary Examiner*—John F. Terapane
*Assistant Examiner*—J. E. Thomas
*Attorney, Agent, or Firm*—Margaret C. Bogosian; Paul A. Gottlieb; Judson R. Hightower

[57] ABSTRACT

The present invention involves labeling monoclonal antibodies with intermediate half-life radionuclides which decay to much shorter half-life daughters with desirable high energy beta emissions. Since the daughter will be in equilibrium with the parent, it can exert an in-situ tumoricidal effect over a prolonged period in a localized fashion, essentially as an "in-vivo generator". This approach circumvents the inverse relationship between half-life and beta decay energy. Compartmental modeling was used to determine the relative distribution of dose from both parent and daughter nuclei in target and non-target tissues. Actual antibody biodistribution data have been used to fit realistic rate constants for a model containing tumor, blood, and non-tumor compartments. These rate constants were then used in a variety of simulations for two generator systems, Ba-128/Cs-128 ($t_{\frac{1}{2}}$=2.4d/3.6m) and Pd-112/Ag-112 ($t_{\frac{1}{2}}$=0.9d/192m). The results show that higher tumor/-background dose ratios may be achievable by virtue of the rapid excretion of a chemically different daughter during the uptake and clearance phases. This modeling also quantitatively demonstrates the favorable impact on activity distribution of a faster monoclonal antibody tumor uptake, especially when the antibody is labeled with a radionuclide with a comparable half-life.

7 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

IN VIVO GENERATOR FOR RADIOIMMUNOTHERAPY

The U.S. Government has rights in this invention pursuant to contract number DE-AC02-76CH00016 between the U.S. Department of Energy and Associated Universities, Inc.

BACKGROUND OF THE INVENTION

Monoclonal antibodies can be used as carriers of radionuclides for tumor imaging and therapy. At present, all therapeutic trials directed at selectively destroying tumors have utilized I-131 as the radionuclide while I-123, I-131, In-111 and Ta-99 m have been coupled with monoclonal antibodies for immunoscintigraphy studies. The approach of using a monoclonal antibody to carry a radionuclide useful in therapy is most beneficial for the treatment of tumors not easily amenable to surgical control, as well as for treatment of early recurrence and of distant metastases. Among the factors that determine if a specific tumor can be destroyed following this technique are the various chemical and biological factors which can influence antibody specificity, stability and kinetics, as well as dosimetric considerations for effective therapy. The choice of the radiolabel is an equally important factor that needs to be optimized to allow the modality to fulfill its potential. I-131 has been used in the therapeutic trials to date because of its ready availability at moderate cost, the ease of halogenation techniques for proteins, and its long history of use in treating thyroid malignancy; these factors do not necessarily signify that it is a prime candidate for use in radioimmunotherapy.

When selecting the radionuclide to be carried by the monoclonal antibdy for radioimmunotherapy applications, the important physical variables include the radionuclide half-life, the type, energy and branching ratio of particulate radiation, and the gamma-ray energies and abundances. It is important to match the physical half-like of the radionuclide with the antibody's in vivo pharmacokinetics. If the half-life is too short, most decay will have occurred before the monoclonal antibody has reached maximum tumor/background ratio. Conversely, if the half-life is too long, this results in unwanted radiation dose to other healthy tissues after the labeled monoclonal antibody is shed from the tumor. It is important to consider the type of particulate emission. Auger and low-energy conversion electrons are potently lethal due to direct ionization and molecular disruption following induced Coulomb explosions. However, this effect can only be realized with intranuclear localization of the radionuclide because of very short range of the particles. Alpha particles have a high linear energy transfer (LET) which is effective in cell killing, but only in a range of several cell diameters. Beta particles are less densely ionizing and have longer range than alphas so that the distribution requirements are less restrictive for radioimmunotherapy. The gamma-ray energies and abundances are also important physical properties because the presence of gamma rays offers the possibility of external imaging but also adds to the whole body dose.

The main chemical variables to be considered in choosing a radionuclide for therapy with monoclonal antibodies are the radionuclide specific activity achievable, metal-ion contamination, the number of labels per monoclonal antibody molecule obtainable without loss of immunological activity, and the stability of the radionuclide-protein bond.

These physical and chemical factors must be viewed in light of available biological information which shows variation in antibody uptake, macro and microdistribution, and kinetics depending on the particular antibody, the variability of antigenic expression in the tumor, its size and stage. Antibodies usually require 1–3 days to reach maximum target to non-target uptake ratios, with residence times on the tumor ranging between 0.5 and 3 days. It is thus most advantageous to use an intermediate half-life radionuclide to match the uptake process and residence time of the monoclonal antibody. Thus the eight day half-life of I-131 is too long for optimum radioimmunotherapy. Also, it is well known that deiodination occurs in vivo so that the radionuclide separates from the antibody carrier. Although there may be numerous antigen sites per tumor cell, present evidence indicates a heterogeneous distribution of the monoclonal antibody in most cases. This fact reduces the attractiveness of short-ranged alpha or Auger emitters as radiolabels for antibodies. It is desirable to deliver ionizing radiation with a range close to 1 mm in tissue, as from intermediate to high energy beta particles in order to effect a uniform tumor dose even if the antibody deposition on the tumor is not uniform.

The number of viable candidate radionuclides having both the desired high beta energy and half-life comparable to antibody uptake kinetics is limited by an inverse relationship between half-life and beta decay energy. Therefore, there are only a few radionuclides that have both the desired high beta energy and a several-day half-life. The present invention presents a new approach to radioimmunotherapy that overcomes this restriction of the prior art. This new approach involves labeling monoclonal antibodies with intermediate half-life radionuclides which decay to much shorter half-life daughters with high-energy beta emissions. Since the daughter is in equilibrium with the parent, it can exert an in-situ tumoricidal effect over a prolonged period in a localized fashion, essentially as an "in vivo generator".

DETAILED DESCRIPTION OF THE INVENTION

Figure 1:
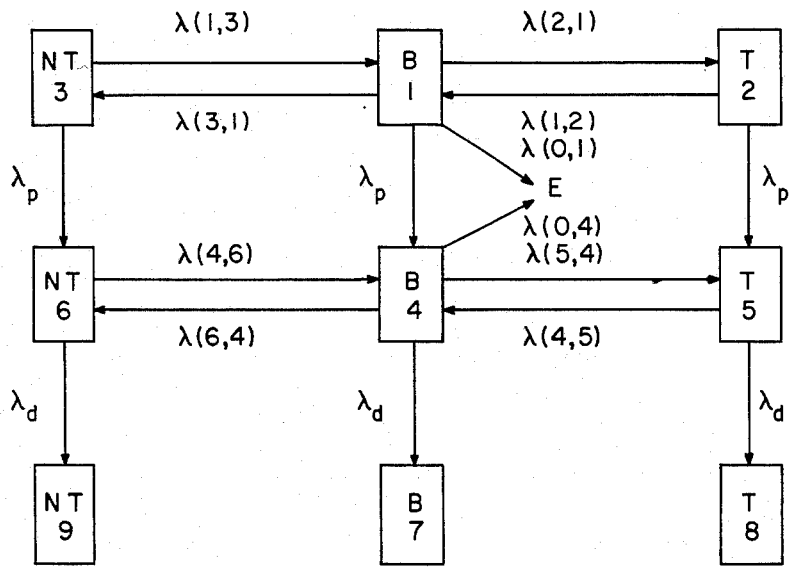
FIG. 1 represents a compartmental model of the in vivo generator. T is the tumor compartment, NT is non-tumor, B is the blood, and E represents excretion to the outside. $\lambda_p$ and $\lambda_d$ are the physical decay constants of parent and daughter respectively. The numbers within the compartments identify the phase of the radioisotope as it distributes throughout the animal system. Thus, for example, for the blood compartments, B1 is the compartment showing distribution of the parent radioisotope in the blood, B4 is the compartment showing distribution of the daughter radioisotope in the blood, and B7 is the compartment showing distribution of the decay products of the daughter in the blood.

The present invention provides a new approach to radioimmunotherapy. Monoclonal antibodies are labeled with intermediate half-life radionuclides which decay in the body to much shorter half-life daughters that emit high energy beta emissions. The equilibrium between the parent and the daughter radionuclides produces the equivalent of an in vivo generator for the desired amount of radiation emission to selectively destroy the targeted tumor or metastases. The decay of the parent to a radioactive daughter yields an extra radiation dose. The present invention takes advantage of this extra dose by combining it with the dose from the parent to increase the total dose to the tumor.

The potential advantages of the "in vivo generator" approach to radioimmunotherapy are that (1) the high-energy beta particles from the daughter can deliver more uniform tumor dose for the same antibody uptake in the lesion; (2) there is more flexibility in choosing the chemical properties and half-life of the antibody label while preserving a high-energy beta emission; and (3) the tumor to background dose ratio may be improved when the daughter exhibits rapid washout from the blood or is chased from the blood during the time the parent-labeled monoclonal antibody is still circulating.

The fate of the daughter nucleus following the uptake of the parent by the tumor is critical; that is, will the daughter translocate to other tissues or organs before decay and how will the parent-daughter system behave in non-target tissue. There are several situations where migration of the daughter away from the parent after localization on the tumor will not be significant. First, if the daughter is very short-lived and chemically different from the parent, it will decay in place at the tumor site faster than metabolic processes can remove it even if the parent-monoclonal antibody bond is broken; an example of such a system would be Ni-66/Cu-66. Second, decay by low-energy isomeric transition can be sufficiently gentle so as to leave the initial molecular bond intact, particularly as there is no change in atomic number and thus parent and daughter have the same chemical structure (e.g., Zn-69m/Zn-69). The candidate system probably should have a small internal conversion coefficient, since the Auger cascade following internal conversion may lead to molecular disruption by Coulomb explosion and electron shake off. In the third case, even if the parent-monoclonal antibody bond is broken, the daughter itself has an affinity for the antibody or tumor tissue and it re-binds to the antibody or tumor. Thus the daughter is retained in the tumor along with the parent (e.g., Pd-112/Ag-112). Table 1 below lists the preferred generator systems that embody these three situations.

TABLE 1

Radionuclides Suitable as "In Vivo" Generator Systems for Use with Monoclonal Antibodies in Radioimmunotherapy

| Parent | | Daughter | | |
|---|---|---|---|---|
| Radionuclide | $T_{\frac{1}{2}}$ | Radionuclide | $T_{\frac{1}{2}}$ | Beta$^-$, MeV (max.) |
| Nickel-66 | 2.3 d | Copper-66 | 5.1 min | 2.63 |
| Zinc-69m | 0.6 d | Zinc-69 | 55 min | 0.90 |
| Palladium-112 | 0.9 d | Silver-112 | 192 min | 3.94 |
| Tellurium-132 | 3.2 d | Iodine-132 | 138 min | 2.12 |
| Barium-128 | 2.4 d | Cesium-128 | 3.6 min | 2.89 ($\beta^+$) |

Of the radionuclides listed in Table 1, $^{132}$Te and $^{128}$Ba have previously been produced at Brookhaven National Laboratory. Tellurium-132 is a product of $^{235}$U fission in the Brookhaven High Flux Beam Reactor and is chemically separated from the $^{235}$U and other fission products by ion exchange on an alumina chromatographic column. The $^{128}$Ba has been prepared by the $^{133}$Cs(p,6n)$^{128}$Ba reaction with 200 MeV protons at the Brookhaven Linac Isotope Producer (BLIP), followed by chemical separation of barium from cesium on a cation exchange column. Nickel-66 could be prepared in low specific activity by double neutron capture on $^{64}$Ni or with high specific activity by the $^{68}$Zn(p,3p)$^{66}$Ni and $^{70}$Zn(p,p$\alpha$)$^{66}$Ni reactions at the BLIP facility. Similarly, $^{69m}$Zn could be produced in low specific activity in the High Flux Beam Reactor by the $^{68}$Zn(n,$\gamma$)$^{69m}$Zn route or with better specific acitivity by the $^{69}$Ga(n,p)$^{69m}$Zn or $^{71}$Ga(p,2pn)$^{69m}$Zn reactions. Finally, $^{112}$Pd could be produced with the $^{114}$Cd(p,3p)$^{112}$Pd reaction at BLIP.

To demonstrate the feasibility of the in vivo generator approach to radioimmunotherapy, the powerful modeling code CONSAM [*Computer Programs in Biomedicine,* 13:111 (1981)] was used to calculate rate constants, simulate experiment, and finally to predict target/non-target ratios. This approach permits great flexibility in testing the effects on biodistribution of different in vivo generator systems and in investigating the interaction of varying antibody uptake kinetics on the choice of the in vivo generator. In this application of CONSAM two radionuclide distributions connected by decay constraints must be tracked. The initial biological model is outlined in the block diagram of FIG. 1.

In effect, this is simply a three-compartment, open model but with extra rate constants connecting the parent distribution to the daughter distribution. It is assumed that initially 100% of the activity is in the blood. The top row of boxes represents the relative atom concentration of the parent; the second row represents the relative atom concentration of the daughter; while the third row is a dummy compartment to handle the product of the daughter decays. The number of atoms in each box of this third row equals the total number of daughter decays in compartments 4, 5 and 6. The lambda values given between the blood, tumor and non-tumor compartments for each form of the radioistope define the equilibrium constant or rate of uptake between the different systems. For example, with the parent radioisotope, the equilibrium constant of this radioisotope between the blood and the tumor is 2,1 while the daughter radioisotope, the equilibrium constant between the blood and the tumor is 5,4.

With this model we calculate the relative dose delivered to each compartment by the parent and separately by the daughter. This simulation has been performed for the $^{66}$Ni/$^{66}$Cu and $^{112}$Pd/$^{112}$Ag systems, which have been chosen as examples of a very short-lived daughter ($t_{\frac{1}{2}}$=5.1 m) and a longer lived daughter ($t_{\frac{1}{2}}$=192 m). The actual physical decay constant were used for $\lambda_p$ and $\lambda_d$.

This modeling has demonstrated that there will not be significant migration away from a tumor by a very short lived daughter radionuclide. Improvement in tumor/blood ratio is quantitatively demonstrated when the antibody tumor uptake is more rapid and it clears from the blood rapidly. It is confirmed that antibody accumulation in the tumor improves when the radionuclide physical half-life is matched with the antibody uptake time. The in-vivo generator approach can achieve improvement in tumor/blood ratio with a fast clearing daughter radionuclide.

We claim:

1. A method of selectively destroying a tumor using radioimmunotherapy which comprises labeling monoclonal antibodies with intermediate half-life radionuclides which, after administration to the patient, decay to much shorter half-like daughters with high-energy beta emissions.

2. The method of claim 1 wherein the radionuclides that are carried to the tumor site by the monclonal antibodies are selected from the group consisting of

| Parent Radionuclide | Daughter Radionuclide |
|---|---|
| Nickel-66 | Copper-66 |
| Zinc-69m | Zinc-69 |
| Palladium-112 | Silver-112 |
| Tellurium-132 | Iodine-132 |
| Barium-128 | Cesium-128 |

3. The method according to claim 1 wherein the radionuclide system employed is Ni-66/Cu-66.

4. The method according to claim 1 wherein the radionuclide system employed is Zn-69m/Zn-69.

5. The method according to claim 1 wherein the radionuclide system employed is Pd-112/Ag-112.

6. The method according to claim 1 wherein the radionuclide system employed is Te-132/I-132.

7. The method according to claim 1 wherein the radionuclide system employed is Ba-128/Cs-128.

* * * * *